(12) United States Patent
Priest

(10) Patent No.: US 8,408,481 B1
(45) Date of Patent: Apr. 2, 2013

(54) MOBILE FRAGRANCE-DISPENSING DEVICE RESEMBLING A PET

(76) Inventor: James C. Priest, Washington, DC (US)

( * ) Notice: Subject to any disclaimer, the term of this patent is extended or adjusted under 35 U.S.C. 154(b) by 358 days.

(21) Appl. No.: 12/888,885

(22) Filed: Sep. 23, 2010

(51) Int. Cl.
*B05B 9/00* (2006.01)

(52) U.S. Cl. .............................. 239/147; 239/71; 239/72

(58) Field of Classification Search .................. 239/34, 239/146, 147, 722, 70, 71, 72; 422/291, 422/120, 123, 105
See application file for complete search history.

(56) References Cited

U.S. PATENT DOCUMENTS

| | | |
|---|---|---|
| 6,089,947 A | 7/2000 | Green |
| 6,520,826 B2 | 2/2003 | Spector |
| 6,749,479 B2 | 6/2004 | Vick |
| 6,901,693 B1 | 6/2005 | Crowe |
| D570,929 S | 6/2008 | Gibson |
| 7,837,958 B2 * | 11/2010 | Crapser et al. ................ 422/291 |
| 2009/0209284 A1 | 8/2009 | Kim et al. |

* cited by examiner

*Primary Examiner* — Davis Hwu

(57) ABSTRACT

A mobile fragrance-dispensing device resembling a pet. The device features a base with an inner cavity for storing a fragrance canister, a microprocessor, wheels disposed on the ends of the legs on the base, and a motor with steering mechanism operatively connected to each wheel. A dispenser system is fluidly connectable to the fragrance canister. The dispenser system functions to spray fragrance from said fragrance canister when activated. A motion sensor is disposed on the head of the base, wherein when the motion sensor is activated the microprocessor activates the dispensing system for a certain length of time.

1 Claim, 4 Drawing Sheets

MOBILE FRAGRANCE-DISPENSING DEVICE RESEMBLING A PET

FIELD OF THE INVENTION

The present invention is directed to a device that dispenses fragrances, more particularly to a fragrance dispenser designed to resemble a pet such as a dog, cat, bird, rabbit, snake, or the like. The dispenser is mobile and can move from room to room.

BACKGROUND OF THE INVENTION

Air freshening systems are commonly used in households. For example, many individuals use fragrance dispensers that plug into an electrical outlet. The present invention features a mobile fragrance-dispensing device that can move room to room (or remain stationary if desired). The device is designed to resemble a pet including but not limited to a dog, a cat, a rabbit, a mouse, a snake, or a bird. The device provides a entertaining and pleasing means of keeping an entire house smelling fresh.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features a mobile fragrance-dispensing device. The device may comprise a base comprising a head portion, a torso portion, and legs, an inner cavity is disposed in the torso portion, the inner cavity is adapted to hold a fragrance canister, the head portion is removably or pivotally attached to the torso portion so as to move between at least an open position and a closed position respectively allowing and preventing access to the inner cavity in the torso portion; a microprocessor disposed in the base; wheels disposed on ends of each of the legs or on a bottom surface of the torso portion; a motor with steering mechanism operatively connected to each wheel and to the microprocessor, the motor with a steering mechanism functions to move and steer the wheels; a dispenser system disposed on the head portion of the base and operatively connected to the microprocessor, the dispenser system is fluidly connectable to a fragrance canister disposed in the inner cavity of the torso portion, the dispenser system functions to spray fragrance from said fragrance canister when activated; a motion sensor disposed on the head of the base, the motion sensor is operatively connected to the microprocessor, the microprocessor is adapted to receive an input signal from the motion sensor when the motion sensor senses motion whereupon the microprocessor generates a first output command to the dispensing system to activate the dispensing system to cause the dispensing system to spray fragrance from the fragrance canister for a first length of time; a power source operatively connected to the microprocessor, the motor with steering mechanism, and the dispenser system; and an on/off switch for turning on and off the device.

In some embodiments, the base is designed to resemble a dog, a cat, a rabbit, a mouse, a snake, or a bird. In some embodiments, the base further comprises a tail. In some embodiments, the first length of time is 0.5 seconds, 1 second, 2 seconds, 3 seconds, 4 seconds, or more than 4 seconds. In some embodiments, the power source is a battery or an electrical outlet. In some embodiments, the battery is a rechargeable battery. In some embodiments, device further comprises a speaker component operatively connected to the microprocessor, the microprocessor has a memory component for storing pre-programmed sounds, wherein the speaker component functions to emit sounds when activated. In some embodiments, when the microprocessor receives the input signal from the motion sensor, the microprocessor generates a second output command to the motor with steering mechanism to cause the motor with steering mechanism to move the wheels thereby moving the device.

DESCRIPTION OF PREFERRED EMBODIMENTS

Referring now to FIGS. 1-6, the present invention features a mobile fragrance-dispensing device 100 that can move room to room (or remain stationary if desired). The device 100 of the present invention is designed to resemble a pet including but not limited to a dog (see FIGS. 1-4), a cat, a rabbit, a mouse, a snake (see FIG. 6), or a bird.

The mobile fragrance-dispensing device 100 of the present invention comprises a base 110 that resembles a pet. For example, the base 110 comprises a head portion, a torso portion, and optionally legs and/or a tail (e.g., the snake version would not have legs). An inner cavity is disposed in the torso portion. The inner cavity is adapted to hold a fragrance canister 180. Fragrance canisters are well known to one of ordinary skill in the art. The head portion may be removably attached to the torso portion so as to move between an open position and a closed position, respectively allowing and preventing access to the inner cavity in the torso portion. This allows a user to remove and replace a canister in the inner cavity (e.g. to change fragrances, etc.).

Figure 6:
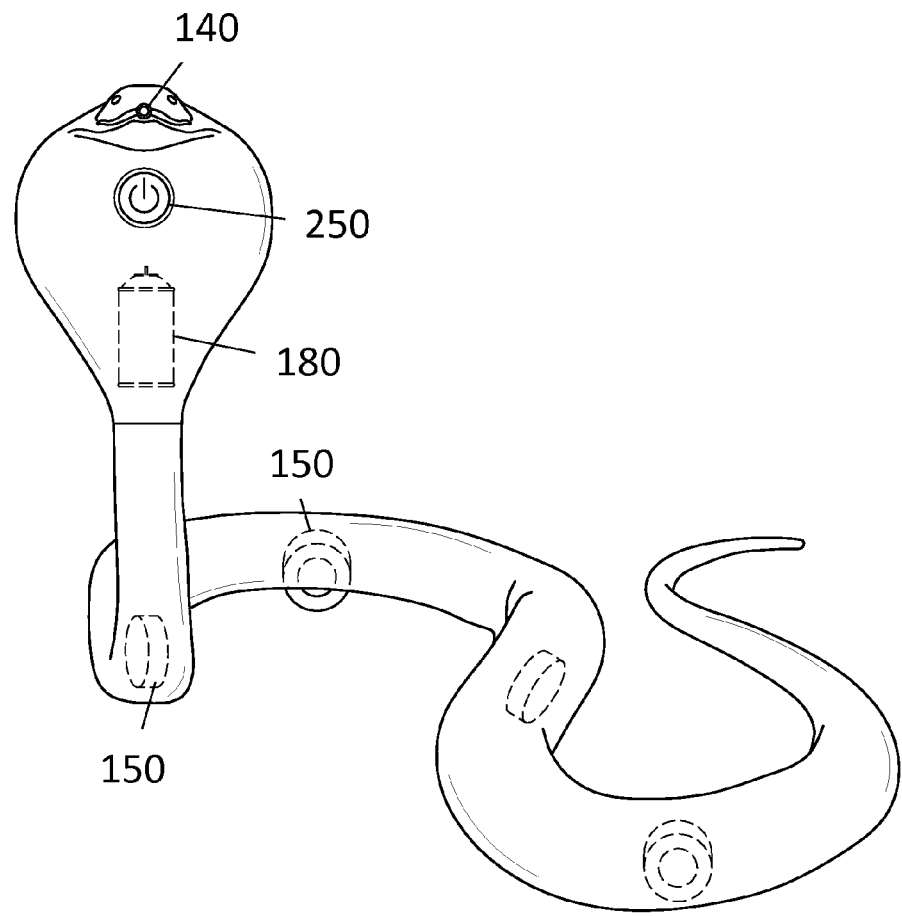
FIG. 6 is a perspective view of an alternative embodiment of the mobile fragrance-dispensing device of the present invention.

As shown in FIGS. 1-4, wheels 150 are disposed on the ends of the legs. The wheels 150 allow the device 100 to move, for example from one room to another. As shown in FIG. 6, wheels 150 may be disposed on the bottom of the torso portion, for example if the device 100 is designed to resemble a snake. The wheels 150 are each operatively connected to a motor with a steering mechanism, which functions together to move and steer the wheels 150. Motors and steering mechanisms for wheels are well known to one of ordinary skill in the art.

Figure 1:
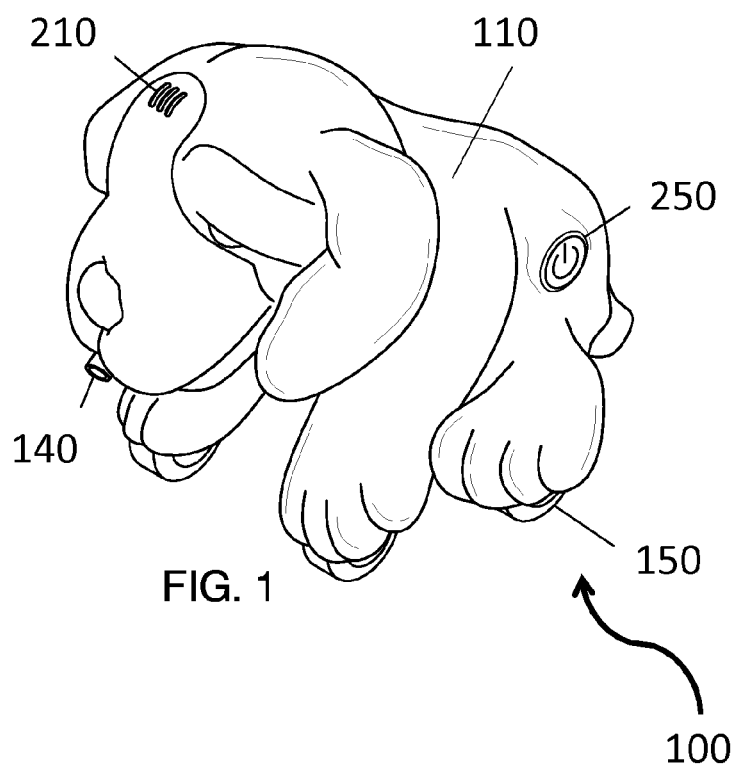
FIG. 1 is a perspective view of the mobile fragrance-dispensing device of the present invention.
Figure 2:
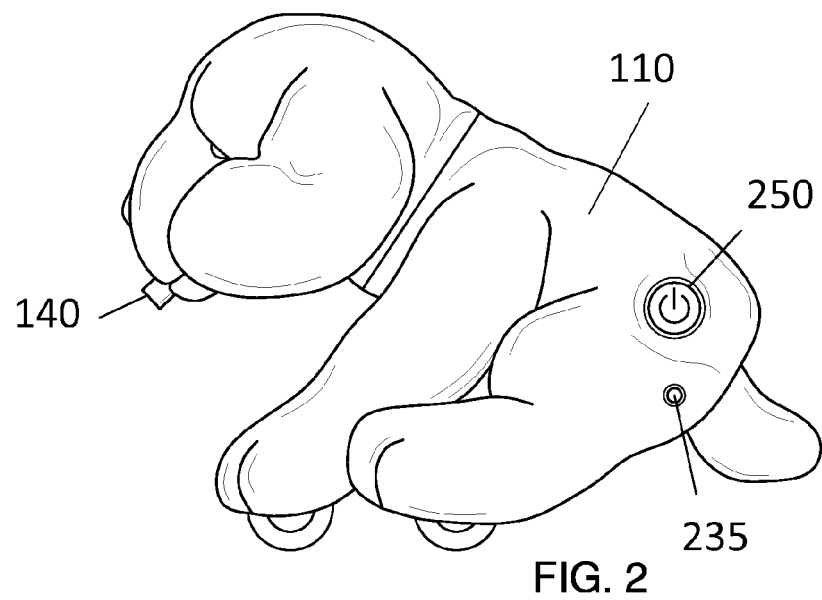
FIG. 2 is a side view of the mobile fragrance-dispensing device of FIG. 1.
Figure 3:
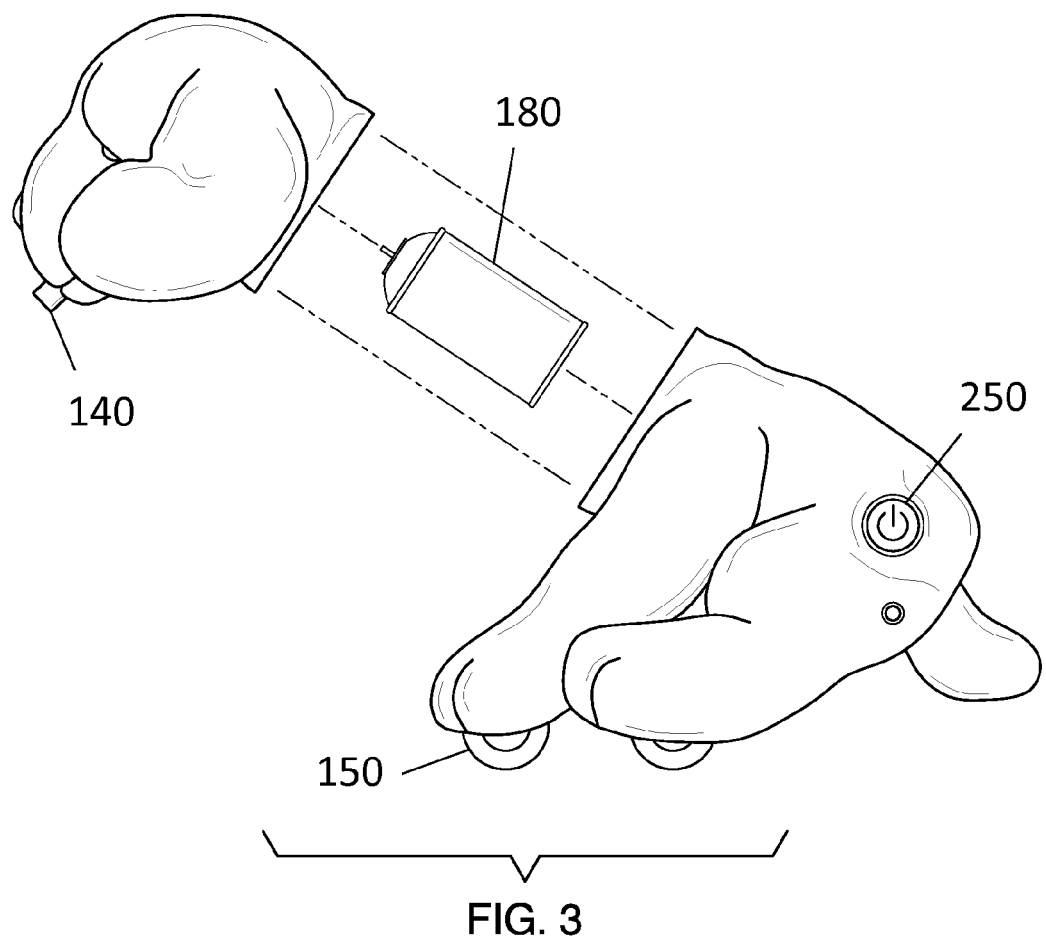
FIG. 3 is an exploded view of the mobile fragrance-dispensing device of FIG. 1.
Figure 4:
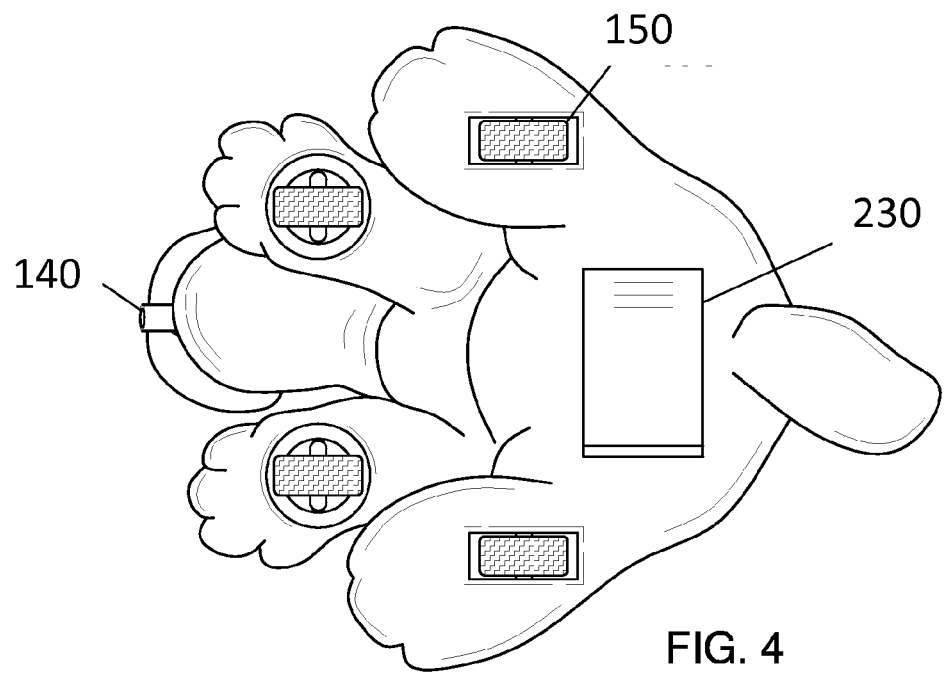
FIG. 4 is a bottom view of the mobile fragrance-dispensing device of FIG. 1.
Figure 5:
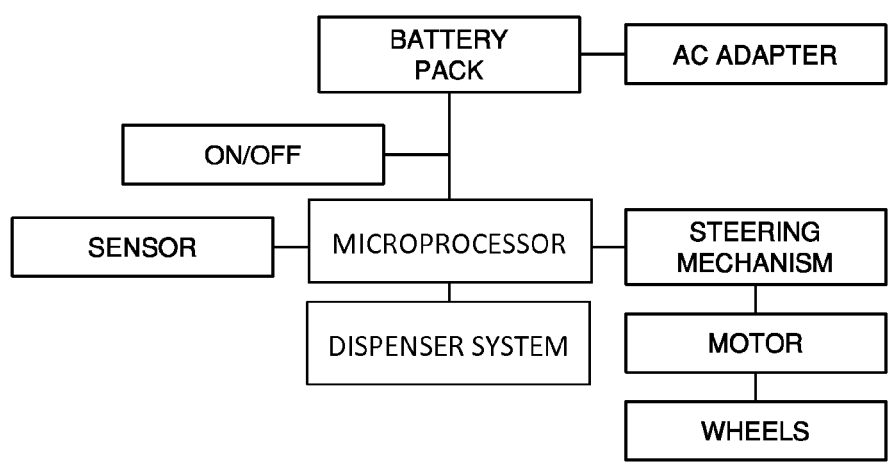
FIG. 5 is a schematic representation of the electrical components of the mobile fragrance-dispensing device of the present invention.

A dispenser system 140 is disposed on the head portion of the base 110 (see FIG. 1, FIG. 2). The dispenser system 140 is fluidly connected to the fragrance canister in the inner cavity of the torso portion and functions to spray the fragrance into the air (when activated). The dispenser system 140 is operatively connected to a microprocessor and a power source (e.g., a battery such as a rechargeable battery in a battery compartment 230). Optionally, the device 100 can be plugged into an electrical outlet via an AC adaptor 235. The AC adaptor 235 may be disposed on the torso portion of the base 110. In some embodiments, the AC adaptor 235 may be used to plug in and recharge the battery in the battery compartment.

In some embodiments, a sensor 210 is disposed on the head of the base 110. The sensor is operatively connected to the microprocessor. In some embodiments, the sensor 210 is a motion sensor configured to detect motion Motion sensors are well known to one of ordinary skill in the art. The microprocessor is adapted to receive an input signal from the motion sensor when the motion sensor senses motion whereupon the microprocessor generates a first output command to the dispensing system to activate the dispensing system. When the dispensing is activated, the dispensing system sprays the fragrance from the canister for a first length of time (e.g., 0.5 seconds, 1 second, 2 seconds, 3 seconds, 4 seconds, more than 4 seconds, etc.).

In some embodiments, when the microprocessor receives the input signal from the motion sensor, the microprocessor generates a second output command to the motor with steering mechanism to cause the motor with steering mechanism to move the wheels thereby moving the device.

The device 100 of the present invention further comprises an on/off switch 250 for turning on and off the device 100. The on/off switch 250 may be operatively connected to the microprocessor and/or the motor and/or the steering mechanism and/or the dispenser system, etc.

In some embodiments, the device 100 further comprises a speaker component operatively connected to the microprocessor (the microprocessor having a memory component for storing pre-programmed sounds). The device 100 may emit sounds (e.g., pet sounds such as meows, barks, etc.) via the speaker.

The device 100 of the present invention may be constructed in a variety of sizes. For example, in some embodiments, the device 100 is between about 10 to 12 inches in length as measured from a first end of the torso portion to a second end of the torso portion. In some embodiments, the device 100 is less than about 10 inches in length. In some embodiments, the device 100 is more than about 12 inches in length.

As used herein, the term "about" refers to plus or minus 10% of the referenced number. For example, an embodiment wherein the device 100 is about 10 inches in length includes a device 100 that is between 9 and 11 inches in length.

The disclosures of the following U.S. Patents are incorporated in their entirety by reference herein: U.S. Pat. No. 6,901,693; U.S. Pat. No. 6,520,826; U.S. Pat. No. 6,089,947; U.S. Pat. No. 6,749,479; U.S. Pat. Application No. 2009/0209284; U.S. Design Pat. No. D570,929.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A mobile fragrance-dispensing device comprising:
 (a) a base comprising a head portion, a torso portion, and legs, an inner cavity is disposed in the torso portion, the inner cavity is adapted to hold a fragrance canister, the head portion is removably or pivotally attached to the torso portion so as to move between at least an open position and a closed position respectively allowing and preventing access to the inner cavity in the torso portion;
 (b) a microprocessor disposed in the base;
 (c) wheels disposed on ends of each of the legs or on a bottom surface of the torso portion;
 (d) a motor with steering mechanism operatively connected to each wheel and to the microprocessor, the motor with a steering mechanism functions to move and steer the wheels;
 (e) a dispenser system disposed on the head portion of the base and operatively connected to the microprocessor, the dispenser system is fluidly connectable to a fragrance canister disposed in the inner cavity of the torso portion, the dispenser system functions to spray fragrance from said fragrance canister when activated;
 (f) a motion sensor disposed on the head of the base, the motion sensor is operatively connected to the microprocessor, the microprocessor is adapted to receive an input signal from the motion sensor when the motion sensor senses motion whereupon the microprocessor generates a first output command to the dispensing system to activate the dispensing system to cause the dispensing system to spray fragrance from the fragrance canister for a first length of time;
 (g) a speaker component operatively connected to the microprocessor, the microprocessor has a memory component for storing pre-programmed sounds, wherein the speaker component functions to emit sounds when activated;
 (h) a power source operatively connected to the microprocessor, the motor with steering mechanism the dispenser system; and
 (i) an on/off switch for turning on and off the device and is operatively connected to the power source.

* * * * *